US008142800B1

(12) United States Patent
Sisco et al.

(10) Patent No.: US 8,142,800 B1
(45) Date of Patent: *Mar. 27, 2012

(54) ORAL HIGH POTENCY CLINICAL ANTI-CRAVING TREATMENT AND METHOD OF USE

(76) Inventors: Tamea Rae Sisco, Centenniel, CO (US); Keith Kenneth Skinner, Centenniel, CO (US); Theodore Keller, Englewood, CO (US)

( * ) Notice: Subject to any disclaimer, the term of this patent is extended or adjusted under 35 U.S.C. 154(b) by 484 days.

This patent is subject to a terminal disclaimer.

(21) Appl. No.: 11/521,848

(22) Filed: Sep. 14, 2006

Related U.S. Application Data

(63) Continuation-in-part of application No. 11/208,467, filed on Aug. 20, 2005, which is a continuation-in-part of application No. 10/025,273, filed on Dec. 18, 2001.

(51) Int. Cl.
*A23L 1/302* (2006.01)
*A23L 1/304* (2006.01)
*A23L 1/305* (2006.01)

(52) U.S. Cl. ......... 424/400; 514/5.5; 514/474; 514/561; 424/630; 424/639; 424/641; 424/643; 424/655; 424/681; 424/702; 536/26.1; 607/900; 426/648

(58) Field of Classification Search ............... None
See application file for complete search history.

(56) References Cited

U.S. PATENT DOCUMENTS

| | | | |
|---|---|---|---|
| 3,697,287 A | 10/1972 | Winitz | |
| 4,005,190 A * | 1/1977 | Mader et al. | 424/679 |
| 4,282,863 A | 8/1981 | Beigler | |
| 4,337,246 A | 6/1982 | Iwagiri et al. | |
| 4,357,343 A | 11/1982 | Madsen et al. | |
| 4,528,197 A * | 7/1985 | Blackburn | 514/552 |
| 4,650,789 A | 3/1987 | Pollack | |
| 4,761,429 A | 8/1988 | Blum | |
| 4,897,380 A | 1/1990 | Pollack et al. | |
| 5,013,752 A | 5/1991 | Dobbins | |
| 5,189,064 A | 2/1993 | Blum | |

(Continued)

FOREIGN PATENT DOCUMENTS

DE 4206422 A1 * 9/1993

(Continued)

OTHER PUBLICATIONS

Singhal, Bhim; Lalkaka, Jimmy; Sankhla, Charu; Epidemiology and treatment of Parkinson's disease in India; 2003; Elsevier, Parkinsonism and Related Disorders, 9 (2003) pp. S105-S109.*

(Continued)

*Primary Examiner* — Cherie M Woodward
*Assistant Examiner* — Ivan Greene
(74) *Attorney, Agent, or Firm* — Fraser Clemens Martin & Miller LLC; J. Douglas Miller

(57) ABSTRACT

A practical high potency anti-craving oral medication or combined oral/IV drip medication is disclosed which comprises three components: a group of amino-acid substances, a group of vitamin substances, and a group of minerals, wherein each substance is selected for maximum efficacy in the body of an individual suffering from substance abuse disorder as opposed to the body of a healthy individual. The ingredients of the invention are selected to cooperate in easing metabolization in the bodies of individuals suffering the various medical conditions associated with substance abuse. The ingredients are provided orally to ease administration and to provide convenient use by patients: the oral medication may be a maintenance dosage or a corrective dosage.

3 Claims, 7 Drawing Sheets

Combined IV Drip and Short-Term Bolus Therapies

U.S. PATENT DOCUMENTS

| | | | |
|---|---|---|---|
| 5,824,684 A | 10/1998 | Viner | |
| 5,935,975 A | 8/1999 | Rose et al. | |
| 6,057,368 A | 5/2000 | Dewey et al. | |
| 6,132,724 A | 10/2000 | Blum | |
| 6,733,797 B1 * | 5/2004 | Summers | 424/728 |
| 6,955,873 B1 * | 10/2005 | Blum | 435/6 |
| 2002/0172721 A1 * | 11/2002 | Boulos et al. | 424/646 |

FOREIGN PATENT DOCUMENTS

| | | | |
|---|---|---|---|
| EP | 558960 A1 * | 9/1993 | |
| WO | WO 9848785 A3 * | 11/1998 | |
| WO | WO 99/61038 A1 * | 5/1999 | |
| WO | WO 99/61038 * | 12/1999 | |
| WO | WO 0126642 A2 * | 4/2001 | |
| WO | WO 03/017784 A1 * | 8/2001 | |
| WO | WO 2004039385 A2 * | 5/2004 | |

OTHER PUBLICATIONS

Derwent Abstract of DE 4,206,422 A1; Derwent Information Ltd; pp. 1-4.*

Sayette, Michael A.; Shiffman, Saul; Tiffany, Stephen T.; Niaura, Raymond S.; Martin, Christopher S.; Shadel, William G.; Methodological Approaches to Craving Research: The measurement of drug craving; 2000; Carfax Publishing, Taylor & Francis Ltd; Addiction, vol. 95, supplement 2, pp. S189-S210.*

Shiffman, Saul; Human Models in Craving Research: Comments on Craving; 2000; Carfax Publishing, Taylor & Francis Ltd; Addiction, vol. 95, supplement 2, pp. S171-S175.*

Tiffany, Stephen T.; Carter, Brian L.; Singleton, Edward G.; Methodological Approaches to Craving Research: Challenges in the manipulation, assessment and interpretation of craving relevant variables; 2000; Carfax Publishing, Taylor & Francis Ltd; Addiction, vol. 95, supplement 2, pp. S177-S187.*

JournalSeek description of the "Journal of Social Work Practice in the Addictions" retrieved from <journalseek.net/cgi-bin/journalseek/journalsearch.cgi?field=issn&query=1533-256X> on Apr. 10, 2010, p. 1.*

Robinson, Terry E.; Berridge, Kent C.; "The psychology and neurobiology of addiction: an incentive-sensitization view," 2000, Taylor & Francis Ltd., Addiction, vol. 95, Supplement 2, pp. S91-S117.*

Drummond, D. Colin; Litten, Raye Z.; Lowman, Cherry; Hunt, Walter A.; "Craving research: future directions," 2000, Taylor & Francis Ltd., Addiction, vol. 95, Supplement 2, pp. S247-S255.*

Blum, Kenneth; Rassner, Michael; Payne, James E.; "Neuro-nutrient therapy for compulsive disease: rationale and clinical evidence," 1990, International Publishing Group, Addiction & Recovery, vol. 10, No. 2, p. 12 (supplied as Dialog® search file-full text, pp. 1-7).*

Newmeyer, John; Inaba, Barryl; Smith, David E.; Waldorf, Gary E.; Levine, Stephen A.; "Efficacy of Buffered Ascorbate Compound (BAC) in the Detoxification and Aftercare of Clients Involved in Opiate and Stimulant Abuse," From the Haight-Ashbury Free Medical Clinic, Jul. 1983; Jun. 1999 Focus on Allergy Research Group newsletter, pp. 1-5.*

Wolffgramm, J.; Galli, G.; Thimm, F.; Heyne, A.; "Animal models of addiction: models for therapeutic strategies?," 1999, Springer-Verlag; Journal of Neural Transmission, vol. 107, pp. 649-668.*

Page, Linda; "Stress & Energy: Reduce Your Stress & Boost Your Energy," 1999, Traditional Wisdom Inc.; pp. 58-65 (supplied as pp. 1-9).*

Derwent Abstract of EP 0558960 A1; Derwent Accession No. 1993-281577, (1993); Derwent Information Ltd; pp. 1-4.*

Blum et al.; "Reduction of both drug hunger and withdrawal against advice rate of cocaine abusers in a 30-day inpatient treatment program by the neuronutrient Tropamine™", 1988, Current Therapeutic Research, vol. 43, No. 6, pp. 1204-1214.*

Blum et al.; "Enkephalinase Inhibition and Precursor Amino Acid Loading Improves Inpatient Treatment of Alcohol and Polydrug Abusers: Double-Blind Placebo-Controlled Study of the Nutritional Adjunct SAAVE™", 1989, Alcohol, vol. 5, pp. 481-493.*

Blum et al.; "Reward Deficiency Syndrome"; 1996; American Scientist, vol. 84, No. 2, p. 132(7-pgs.), (pp. 1-13 as supplied).*

The FDA Label for "Aminosyn II With Electrolytes"; retrieved from <http://dailymed.nlm.nih.gov/dailymed/about.cfm> on Jul. 1, 2011; pp. 1-8.*

Stadelman et al.; "Egg Science and Technology", 4th ed., 1995; The Haworth Press Inc.; pp. 177-183.*

* cited by examiner

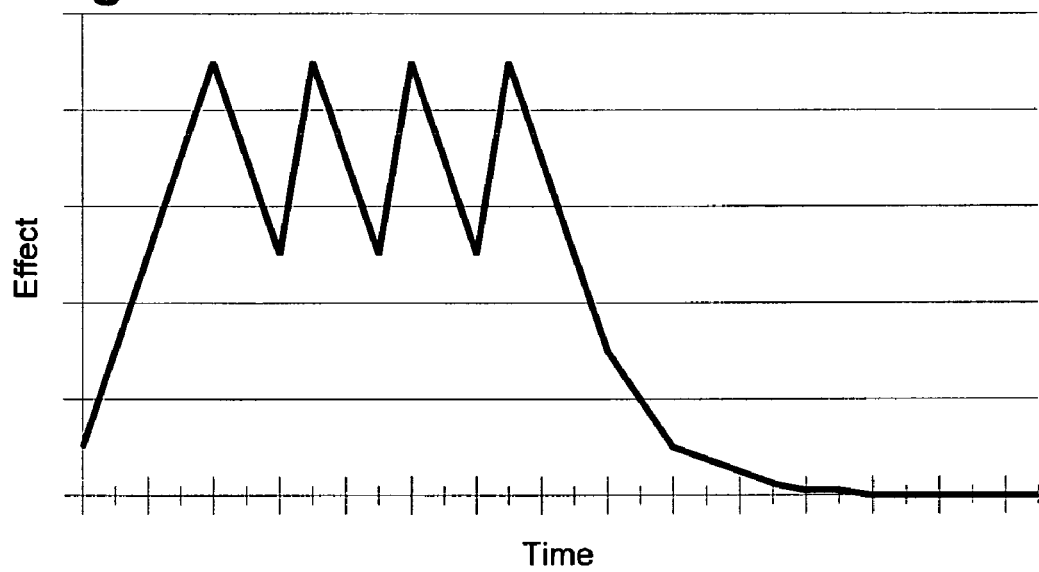

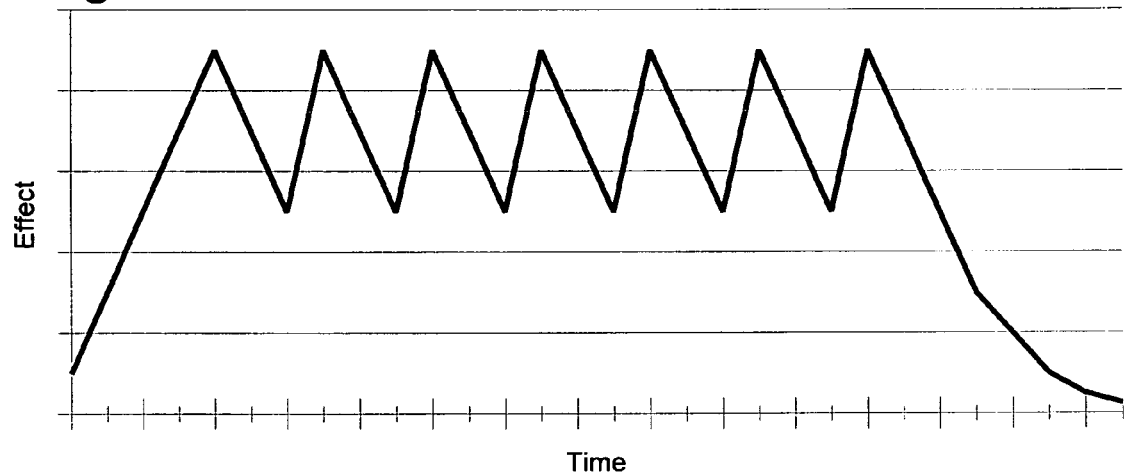
Fig. 3C - Increased Time and Concentration

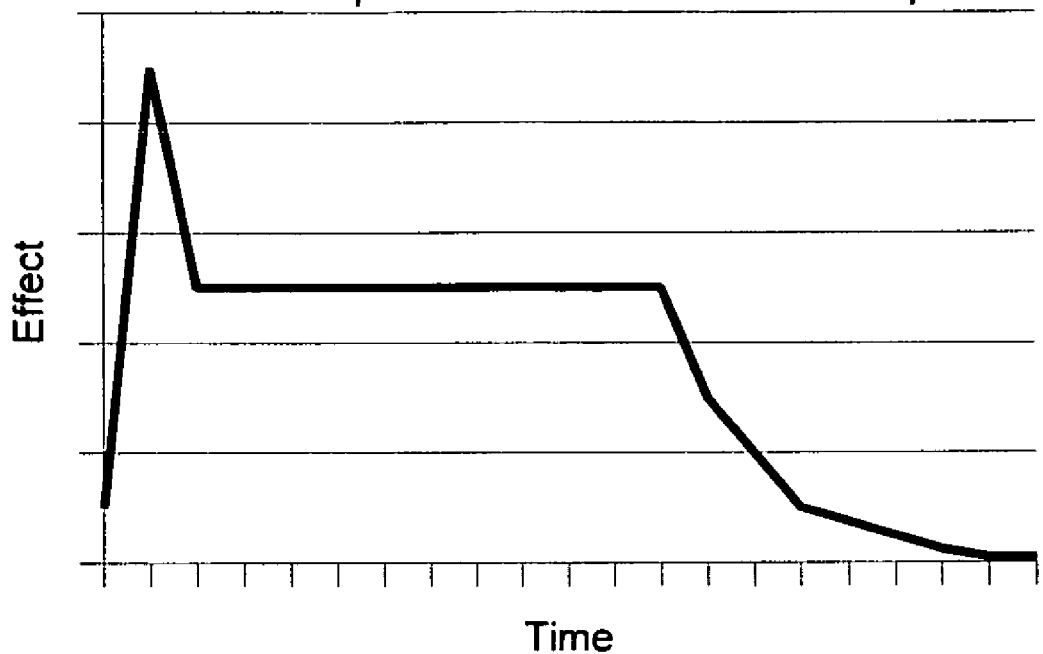

ORAL HIGH POTENCY CLINICAL ANTI-CRAVING TREATMENT AND METHOD OF USE

REFERENCE TO RELATED APPLICATION

This application is a continuation-in-part application of U.S. application Ser. No. 11,208,467 having the same title and filed Aug. 20, 2005, the entire disclosure of which is incorporated herein by the reference, which is a continuation-in-part application of U.S. application Ser. No. 10/025,273 filed Dec. 18, 2001.

FIELD OF THE INVENTION

The invention relates to anti-craving treatments for patients suffering from substance abuse disorders (SAD). More particularly, the invention relates to an amino-acid anti-craving treatment in both corrective and maintenance regimes, the treatment offering high efficacy in patients having those health problems common among substance abuse sufferers.

STATEMENT REGARDING FEDERALLY FUNDED RESEARCH

This invention was not made under contract with any agency or body of the United States Federal Government.

BACKGROUND OF THE INVENTION

The societal consequences of the substance abuse disorders (SADs), cumulated over many millions of individuals, are well known. Every year, hundreds of thousands of lives are simply ended by substance abuse and related social problems, millions of lives are mined, and many millions of lives are adversely impacted directly and even more are impacted indirectly. The financial impact on society is almost as staggering: billions of productive days lost to SAD and secondary effects. This serves as one motivation for theoretical and laboratory medical research into the causes and cures for substance abuse disorders.

Horrendous as they are, such statistics pale in comparison to the results of substance abuse when the impact is measured on any given individual. Affected individuals usually suffer an almost total disruption of every facet of their previous lives: relationships destroyed, families disrupted or ripped apart, finances shattered, reputations mined, careers ended and the list goes on. For those on the "front lines" of addiction treatment, this serves as a very urgent motivation for practical and clinical medical research into the human conditions that lead to substance abuse or addiction. Medical research in the area is thus driven both from the top downwards and from the grass roots upwards.

Biological Bases of Addiction

In the last few decades, it has become increasingly clear on the theoretical side that addiction is in fact either largely or wholly a physiological disorder. Researchers have learned that in a few cases, a small number of genetic variations may be enough to provide an individual with a "predisposition" or "vulnerability" to addiction. It is also becoming clearer that a larger number of milder genetic variations may conspire together to create the same effect. Commonly abused substances themselves alter the function of the brain's normal pleasure response system, apparently as a result of the brain's adaptation to the substance. In fact, regardless of cause, the mere usage of certain chemicals (for example cocaine, alcohol, nicotine and morphine) is linked with changes in the brain's functioning and the associated craving for those substances. The result seems to be a grouping of very similar biochemical neuronal conditions which adversely impact the brain's pleasure responses. The term "Reward Deficiency Syndrome" (RDS) has been coined to describe these disorders. Estimates of the number of individuals that display RDS range as high as one third of the population. U.S. Pat. No. 6,132,724, issued on Oct. 17, 2000 to Blum and entitled "Allelic Polygene Diagnosis of Reward Deficiency Syndrome and Treatment" provides a great deal of background material on RDS and the probable genetic causes thereof.

The brain's neurotransmitter chemicals, receptor cells for those chemicals, and related systems regulating production and maintenance of the appropriate level of these neurotransmitters are at the center of this reward deficiency syndrome. For example, serotonin and dopamine have been implicated in this process: alterations in the metabolic cycle of these substances is part and parcel of substance abuse behavior and recovery therefrom. Dopamine levels may be reduced by substance abuse, and dopamine reception by the neurons may be reduced by substance abuse, thus forming one component of the craving for the substance. It is also possible that the individuals addicted to the substances in question had poor dopamine reception prior to the abuse behavior, and that the poor reception was part of the reason that the individual succumbed to the disease. Following this theory, it is believed that drug abuse breaks down or occupies dopamine connections of the brain, leading to addiction problems. More specifically it is known that dopamine release can be induced by application of precursor amino-acids, thus assisting in reduction of craving. In addition, it is also known that In addition to dopamine and serotonin, GABA and the opioid peptides are also believed to play a complex role in the reward process. For example, GABA may regulate dopamine release. Studies in rats and mice having a susceptibility to the abuse alcohol show low levels of serotonin and dopamine and increased levels of GABA and opioid peptides. One example of a patent for a medication which acts on the dopamine levels in the brain is U.S. Pat. No. 6,057,368, issued to Dewey et al on May 2, 2000 for "Treatment of Addiction and Addiction-Related Behavior." The medication taught by the '368 patent uses gamma vinyl GABA as an agent, and is not untypical of modern developments in treatment.

Treatment Regimes

In the past, addiction was treated as a moral or personal flaw, not a physiological condition. Thus treatment often was nonexistent. As the need for therapy became clear, early treatment regimes were instituted. Treatment often consisted of psychological support for the patient, or occasionally, not even that: in some nations, treatment consisted of forcing the individual to undergo "cold turkey" withdrawal in a prison cell. While psychological support for the patient is a necessary part of any treatment regime, methods based only on such support or m a worst case scenario on simultaneous deprivation of both substance and support were only partially successful.

There have been actual attempts to treat the underlying physical symptoms of the problem. Two methods involved in these early attempts to treat the physiology of RDS were the application of agonists and the application of antagonists.

Agonists are substances which themselves are received or otherwise stimulate reception of a neurotransmitter in the neurons, resulting in a "substitution" of one substance, the abused substance, with another: its agonist. The theory is that the craving will be satiated without recourse to the abused substance. Methadone is an example of a heroin agonist. While some positive results were achieved, it is uncertain if methadone treatment actually offered a higher rate of success than psychological support. Numerous "nicotine patches" are offered as a type of substitution therapy for nicotine addiction: while the agonist was in fact the abused substance nicotine, many other dangerous chemicals found in cigarettes, cigars and chewing tobacco are eliminated. In addition, the patient can control the dosage self administered, offering the opportunity to gradually end the nicotine dependency. However, most agonist therapies to date have suffered from a common weakness: they attempt to satisfy craving by replacing the desired substance with some other desirable substance, rather than by offering the patient's body the ability to return the patient's neurochemistry to a healthy state. Obviously, reduction of the craving would be preferable to merely satisfying it. In addition, certain agonist can themselves become addicting, and the patient's tolerance can increase, resulting in the need for higher dosages of the medication, not lower.

Antagonists, on the other hand, actually reduce the potency of the abused substance, resulting in reduced reward for its administration. Naltrexone is an example of a substance which blocks the effects of heroin. In this case, the operative theory is that with reduced reward, the individual will eventually cease to abuse the substance. However, the craving itself is not reduced, merely left unsatisfied by administration of the abused substance. Unfortunately, the action of blocking the effects of the abused substance is rather similar to simply denying the patient the substance in the first place: the craving remains, unsatiated. Worse, the patient's level of well-being spends long periods of time in the "anhedonia" or "dysphoric" (unhappy) phase of the abuse cycle, possibly inflicting as much pain as a "cold turkey" incarceration would have, and demonstrating no overwhelming reduction in the rate of recidivism. Even worse, the internal blockade of the abused substance may simply lead the sufferer to attempt greater dosages of it, with potentially catastrophic results. U.S. Pat. No. 5,824,684 issued to Viner on Oct. 20, 1998, may be taken as an example of a medication including an antagonist agent.

There have also been attempts to combine the agonist and antagonist therapies: See U.S. Pat. No. 5,935,975, issued to Rose et al on Aug. 10, 1999, for "Agonist-Antagonist Combination to Reduce the Use of Nicotine and Other Drugs". In the method, the agonist (or even the substance abused) is administered to the patient. At the same time or shortly thereafter, the subject is administered the antagonist to the abused substance. In theory, the approach leaves a lesser number of receptors available to respond to the abused substance, while at the same time minimizing the negative effects of a pure antagonist therapy. (See col. 4. lines 38-42.)

Each of these two methods and even combined methods such as the '975 patent do not attempt to return the neurotransmission system to a normal state. While therapy using an agonist temporarily reduces craving, the reduction is simply due to the administration of the abused substance or another having the same psycho-physiological effects. In no case is the actual source of the craving itself—the brain's neurotransmitter imbalances—really lessened, nor is the brain's reward system moved towards a normal balance.

Thus, new and promising therapies have concentrated on a different approach: craving reduction.

Craving-Reduction Therapies

One example of an attempt to treat substance abuse behavior is U.S. Pat. No. 5,013,752, issued May 7, 1991, entitled "Prevention and Treatment of Alcoholism by the use of Dietary Chromium." While the claim that chromium deficiency is by itself a cause of alcoholism is debatable, the use of chromium has become well established since that time as an ingredient in anti-craving compounds.

Amino-acids have been known for some time as potential agents for dealing with various conditions. U.S. Pat. No. 4,357,343 issued to Madsen, et al on Nov. 2, 1982, entitled "Nutritional Composition for Management of Renal Failure" is a typical example. A recent development in addiction therapy is the use of craving-reduction medications based upon amino-acid precursors of neurotransmitters such as serotonin and dopamine. In this approach, the patient is administered with an oral medication containing substances selected for their ability to promote healthy neurotransmitter function. Certain amino-acids are known to be precursors of the neurotransmitters. For example, the amino-acid 5-hydroxytryptophan is believed to be a precursor of serotonin while the neurotransmitter L-phenylalanine is believed to be a precursor of dopamine. Other amino-acids also function as metabolic precursors of the desired neurotransmitters.

Unfortunately the complexity of the human brain can substantially reduce the efficacy of merely providing a patient with a precursor amino-acid. The reward/pleasure system is not dependent upon any one single biochemical reaction, nor even upon a small number or class of biochemicals, nor does it occur in any one region of the brain. The interactions between the different chemicals in the human anatomy mean that even a subtly different medicinal formulation may have surprising or unexpected results.

For example, certain medicines taught for addiction therapy comprise a single amino-acid. But the interaction of different chemicals within the human anatomy means that this approach may not be efficient, indeed, may not even be effective. In greater detail: the reward/pleasure response in the brain is a complex process in which stimulus in one part of the brain controls stimulus in others, which may in turn lead to stimulation of yet another part of the brain. Each of the steps of release, reception or uptake of neurotransmitters takes place at simultaneously at different locations, and for different substances, and different steps in the neurotransmission cycle may be under the influence of different neurotransmitters or other biochemicals: the release, reception or uptake of neurotransmitters is frequently under the control of other substances: amino-acids, vitamins and minerals. A short example is provided: a low level of a neurotransmitter in the brain can be partially or wholly offset by application of precursor amino-acids which help to build up the level. However, the level of the precursor amino-acids in the brain may be determined by their ability to cross the blood/brain barrier, which in turn may be governed by the amount of a given mineral in the bloodstream, even a mineral normally considered unrelated to the addiction regime. The rate of breakdown and maintenance of the same neurotransmitter in the brain may also be effected or even controlled at that point by the availability of some vitamin or mineral in the system acting upon the enzyme controlling the neurotransmitter. And a mineral which promotes the crossing of the blood/brain barrier by one amino-acid might act to reduce the crossing of the same barrier by other amino-acids. To provide details in this short example: L-tryptophan is a precursor which promotes neurotransmitter activities, while D-phenylalanine promotes neurotransmitter activity by inhibiting enzymatic cleavage. Administration of niacinamide, a form of the vitamin niacin, reduces the premature breakdown of L-tryptophan in the blood stream because tryptophan is typically used in a 60 to 1 ratio to produce niacinamide. Niacinamide later appears to reduce the rate of serotonin breakdown in the brain by inhibiting the action of tryptophan pyrrolase. The mineral calcium assists L-tryptophan to enter the brain, and then further assists conversion of tryptophan to serotonin, but drives other amino-acids into muscle tissue instead. L-tryptophan is desired for its ability to elevate serotonin levels, act as asleep agent, and reduce depression. When a patient is sleeping well and not depressed, the L-tryptophan may actually be removed from alternative embodiments of the present invention. Obviously while L-tryptophan is desirable, it is not desirable to encourage L-tryptophan's action at the expense of the other amino-acids used in the present invention. There are literally hundreds of such interactions taking place, creating a system too complex for present day modeling techniques to interpret.

Thus formulation of amino-acid based anti-craving medications is an unpredictable task, and anti-craving medications tend to involve a spectrum of ingredients designed to assist the combined efficacy or efficiency of the anti-craving effect. Examples of anti-craving compounds show the wide variation in formulations. For example, as referenced previously, U.S. Pat. No. 6,132,724, issued on Oct. 17, 2000 to Blum and entitled "ALLELIC Polygene Diagnosis of Reward Deficiency Syndrome and Treatment" provides a great deal of background material on RDS and the probable genetic causes thereof, and furthermore discloses and claims an oral anti-craving composition comprising a substance which inhibits the enzymatic destruction of a neuropeptidyl opiate, a neurotransmitter-precursor amino-acid, chromium, and either an herbal extract from Rhodiola rosea or huperzine. U.S. Pat. No. 4,761,429 ("Enkephalinase and Endorphinase Inhibitors as Anti-Craving Compositions", issued Aug. 2, 1988) and U.S. Pat. No. 5,189,064 ("Treatment of Cocaine Disorders", issued Feb. 23, 1993) both to the same individual as the '724 patent, disclose craving reduction by means of administering one or more amino-acids which "inhibit the destruction of neuropeptidyl opiates . . . in an amount sufficient to reduce the craving". The same individual (Dr. Kenneth Blum, usually considered a leader in the field) has also stated that he has a pending patent application which was filed on Mar. 21, 2000, (application and number are unavailable to the present applicant) regarding short-term bolus administration of amino-acids and Rhodiola extract.

Another excellent background article may be found in SUBSTANCE AND ALCOHOL ACTIONS/MISUSE, Vol. 3, pp. 231-239, dated 1982, in the name of author Seymour Ehrenpreis, Ph.D., regarding the use of D-phenylalanine and other enkephalinase inhibitors in therapeutic applications. At page 235, this article discusses linkage between development of tolerance to the analgesic actions of opiates and physical dependence with endorphins and states that this "immediately suggests important clinical uses for enkaphalinase inhibitors . . . . This in itself might well inhibit the development of dependence. DPA (D-phenylalanine) or other enkephalinase inhibitors could also be employed to ameliorate symptoms of withdrawal in heroin or morphine addicts."

One barrier to efficient usage of administered amino-acids, albeit a barrier present in all human beings rather than just those suffering from substance abuse disorder, is the blood/brain barrier. U.S. Pat. No. 4,650,789 and U.S. Pat. No. 4,897,380, respectively issued to Pollack and to Pollack, et al, on Mar. 17, 1987 and Jan. 20, 1990, for "Method and Composition for Increasing Production of Serotonin" and "Method and Composition for Relieving Dietary-Related Disorders" also propose amino-acid medications for neurotransmitter re-balancing. These two patents both teach the use of L-tryptophan as the amino-acid, along with ingredients designed to assist it across the blood/brain barrier. However, in order to assist L-tryptophan in crossing the blood/brain barrier, both patents suggest the use of fructose to drive other amino-acids in the patient's blood stream into the muscles, thus increasing the relative concentration of L-tryptophan and speeding its passage to the brain. Obviously, this is counterproductive if the objective is to administer a group of amino-acids.

Another example of this problem is the administration of cyanocobalamin (vitamin B12). While cyanocobalamin is the form of vitamin B12 which is metabolized in oral administration, and thus the form known in the art in anti-craving compositions, it is also a form which must first pass through the metabolic machinery of the liver to become hydroxycobalamin, then be metabolized by the liver a second time in order to become the metabolically active form of the agent vitamin B12. This known process is disadvantageous for use by substance abuse patients, as will be explained below in the detailed description of the present invention.

All of these compositions contain weaknesses in terms of their practical efficiency of use by the body of a substance abuser. In some cases, important components are administered in a form which decreases their ability to be absorbed into the blood stream at all. Some of the same references offer important active agents in forms which are slow or difficult to metabolize in the body of an individual who has abused substances. Other references teach the use of agents such as fructose which assist the use of one amino-acid at the expense of all others. Finally, compounding of numerous amino-acids, vitamins and minerals into a formula suitable for IV administration, with the consequent advantages thereof, is quite difficult. Amino-acid medications via intravenous drip may require the administration of a dozen or more vials of medication. Combinations of numerous ingredients, however, are likely to precipitate or react in storage. This both teaches away from the creation of multiple agent medications and also makes it difficult to find suitable formulas for such agents.

A second issue which arises is that of form of administration. The efficacy of a given medication will be a function of the concentration in the body of the individual achieved by a given method of administration and the time for which that concentration is maintained. Known oral medications are inefficient in terms of the concentration achieved. Direct injection via short-term bolus therapy on the other hand will merely "spike" the desired active agents in the body of the patient without providing a substantial amount of time for the agents to take effect. The knowledge that the active anti-craving agents would quickly depart the metabolic system appears to have caused previous researchers in the field to tend to avoid water soluble forms of the active anti-craving agents.

Oral administration suffers from barriers between administration and brain cell receptor sites, and generally allows lower dosages.

Thus, a need remains for an anti-craving medication which is formulated and administered for high efficacy due to the combination of active agents, but which is also formulated for efficient usage by the body of an individual suffering from the typical conditions of a substance abuser.

The present applicants have previously shown that long time IV drip is one effective way to elevate levels of desirable nutrients in the blood of patients. Building on that, the present application teaches that oral medications, if properly formulated may be used in either a maintenance role (following a corrective course of IV therapy) or in an initial corrective role.

SUMMARY OF THE PRESENT INVENTION

It is therefore yet another aspect, advantage, objective and embodiment of the present invention to provide an anti-craving oral medication for administration to the body of an individual suffering from substance abuse, said medication comprising:
- DL-PHENYLALANINE in the amount of 375 MG;
- L-TYROSINE in the amount of 1375 MG;
- L-GLUTAMINE in the amount of 375 MG;
- GABA in the amount of 51 MG;
- 5-HYDROXYTRYPTOPHAN in the amount of 30 MG; and
- DL-METHIONINE in the amount of 30 MG.

It is therefore a second aspect, advantage, objective and embodiment of the present invention to provide an oral anti-craving medication further comprising:
- VITAMIN C in the amount of 15 MG;
- THIAMINE in the amount of 1 MG;
- RIBOFLAVIN in the amount of 1 MG;
- PYRIDOXINE in the amount of 7 MG;
- FOLIC ACID in the amount of 99 MCG;
- CYANO-COBALAMIN in the amount of 26 MCG;
- BIOTIN in the amount of 7 MCG;
- PANTOTHENIC ACID in the amount of 25 MG;
- CALCIUM in the amount of 128 MG;
- CHROMIUM in the amount of 22 MCG;
- MAGNESIUM in the amount of 25 MG;
- ZINC in the amount of 25 MG; and
- MANGANESE in the amount of 188 MCG.

It is therefore yet another aspect, advantage, objective and embodiment of the present invention to provide an oral anti-craving medication further comprising:
- VITAMIN C in the amount of 7.5 MG;
- THIAMINE in the amount of 500 MCG;
- RIBOFLAVIN in the amount of 500 MCG;
- PYRIDOXINE in the amount of 3.5 MG;
- FOLIC ACID in the amount of 50 MCG;
- CYANO-COBALAMIN in the amount of 13 MCG;
- BIOTIN in the amount of 3.5 MCG;
- PANTOTHENIC ACID in the amount of 12.5 MG;
- CALCIUM in the amount of 64 MG;
- CHROMIUM in the amount of 11 MCG;
- MAGNESIUM in the amount of 12.5 MG;
- ZINC in the amount of 12.5 MG;
- MANGANESE in the amount of 94 MCG;
- SIBERIAN GINSENG in the amount of 2.5 MG;
- GOTU KOLA in the amount of 2.5 MG;
- DMAE in the amount of 2.5 MG;
- MUCUNA PRURIENS in the amount of 2.5 MG; and
- RHODIOLA in the amount of 2.5 MG.

It is therefore yet another aspect, advantage, objective and embodiment of the present invention to provide a multiple administration route anti-craving medication for administration to the body of an individual suffering from substance abuse, said medication comprising:
a) a first course of long term IV therapy having amino acid components, mineral components and vitamin components;
b) a second course of longer term oral medication having:
- DL-PHENYLALANINE in the amount of 375 MG;
- L-TYROSINE in the amount of 1375 MG;
- L-GLUTAMINE in the amount of 375 MG;
- GABA in the amount of 51 MG;
- 5-HYDROXYTRYPTOPHAN in the amount of 30 MG; and
- DL-METHIONINE in the amount of 30 MG.

It is therefore yet another aspect, advantage, objective and embodiment of the present invention to provide a multiple administration anti-craving medication of claim 4, wherein the first course of amino acid components, mineral components and vitamin components further comprises:
in the first component:
- approximately 7.50 grams of D-phenylalanine,
- approximately 7.50 grams of L-phenylalanine,
- approximately 0.05 grams of L-tyrosine,
- approximately 2.4 grams of L-tryptophan,
- approximately 15.0 grams of L-glutathione, and
- water to bring the total volume to 1000 milliliters.

in the second component:
- approximately 2 grams of folic acid,
- approximately 0.4 grams of methylcobolamin,
- approximately 500 grams of ascorbic acid from a beet source,
- approximately 5.0 grams of thiamine hydrochloride,
- approximately 0.4 grams of pyridoxal-5-phosphate monohydrate,
- approximately 0.4 grams of riboflavin-5-phosphate sodium,
- approximately 10.0 grams of niacinamide,
- approximately 20.0 grams of dexpanthenol,
- approximately 10.0 grams of inositol, and
- water to bring the bulk volume to 1000 milliliters.

in the third component:
- approximately 8 grams of magnesium chloride,
- approximately 12.8 grams of zinc sulfate,
- approximately 1.572 grams of cupric sulfate,
- approximately 0.612 grams of manganese sulfate,
- approximately 0.02052 grams of chromic chloride,
- approximately 0.0392 grams of sodium selenite, and
- water to bring the bulk volume to 1000 milliliters.

BRIEF DESCRIPTIONS OF THE DRAWINGS

FIG. 1 is a bar graph showing comparative recidivism rates of the present invention versus counseling only treatment regimes.

FIG. 2, PRIOR ART, is a graph of the effectiveness of short-term bolus therapy as measured by concentrations of active agents versus time.

FIG. 3B is a graph of the effectiveness profile of oral administration in terms of concentrations of active agents versus time for a higher concentration of administrations.

FIG. 3C is a graph of the effectiveness of oral administration in of concentrations of active agents versus time for a higher concentration and longer period of administration.

FIG. 4 is a graph of the effectiveness of combined IV drip therapy and short term bolus therapy, as measured by concentrations of active agents versus time.

Figure 5:
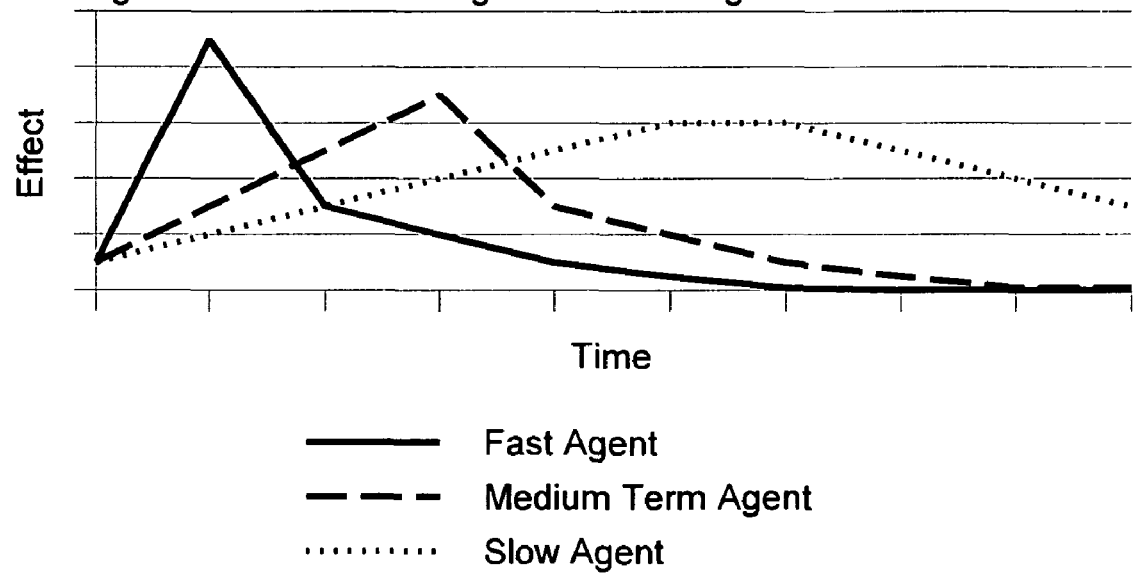

FIG. 5, PRIOR ART, is a graph of the effectiveness of three agents having differing metabolic half-lives when administered simultaneously, as measured by concentrations of the agents versus time.

DETAILED DESCRIPTION OF THE INVENTION

The invention provides an anti-craving medication whose active agents are selected to overcome the physical barriers to efficient use which exist in the bodies of individuals suffering from substance abuse; that is the agents are selected so as to allow efficient use of the medication by such a body of an individual suffering from substance abuse. The result is a formulation for a medication offering high overall efficacy.

The present oral formulation of the invention may be used in a corrective role, particularly using improved methods of delivery now known or later developed. In embodiments, the present formulation of the invention may be used in a maintenance role, that is, following a course of a higher dosage, more efficacious long term IV drip formulation of the invention.

Figure 1:
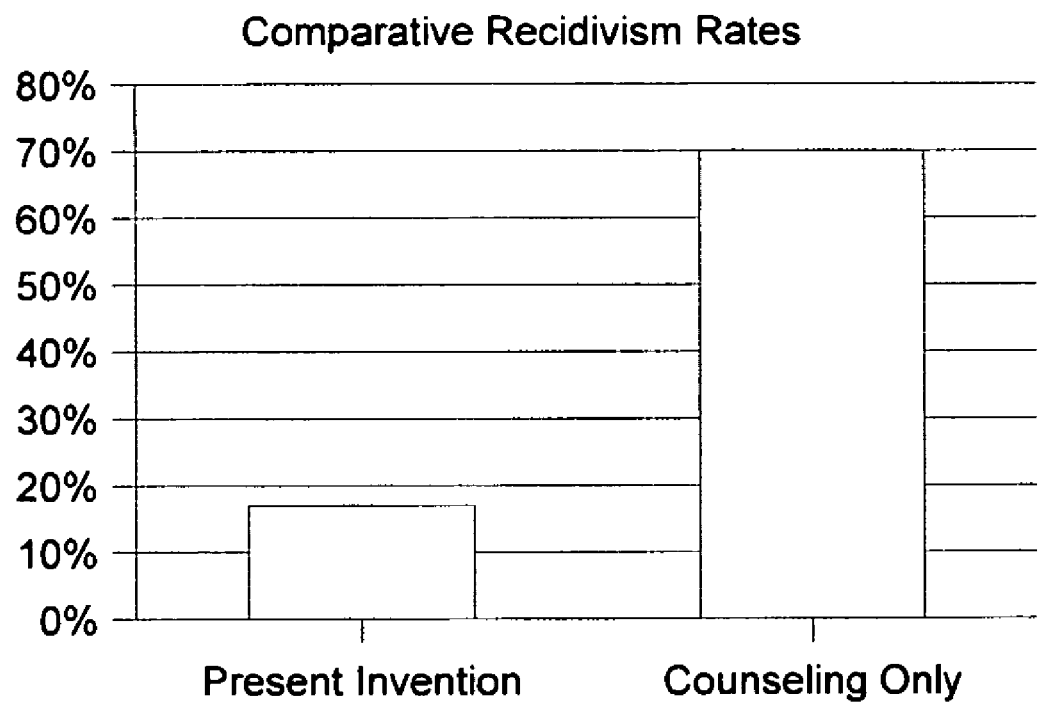

FIG. 1 is a bar graph showing comparative recidivism rates of the IV embodiment of the present invention versus counseling only treatment regimes. Recidivism rate, that is, the percentage of patients treated who return to substance abuse during or after treatment is a key measure of the overall efficacy of substance abuse medications. A lower recidivism rate is therefore much better than a higher recidivism rate. As stated earlier and shown on FIG. 1, counseling alone does not have a very high success rate: fully 70% of patients relapse at least once into substance abuse. While testing and accumulation of statistical data is not complete and the medication of the present invention has not yet been commercialized, the medication of the present invention is considerably superior to this counseling alone: only 17% of patients relapse into substance abuse after treatment with the IV form of the medication of the present formulation.

The medication achieves this by selecting those forms of anti-craving agents which are most usable by a body suffering the disorders pandemic in substance abuse. Such disorders erect several physical barriers to efficient use of normal selections of agents for anti-craving compounds. To list several examples of such physical barriers: the stomach and intestinal linings of substance abusers are often damaged or simply dysfunctional, liver disease is quite prevalent among many types of substance abusers, substance abuse physically deprives the body of necessary nutrients (for example, by overusing the nutrients in the futile attempt to metabolize the abused substances at a rate sufficient to keep pace with the amounts the individual abuses) and psychologically deprives the abuser of the desire to follow proper nutritional guidelines; the poor nutrition endemic in this population then harms the abilities of the body to properly digest food and to utilize these nutrients and to assist the passage of the active agents across the blood/brain barrier, time factors work against the efficient usage of medications by those with substance abuse problems, and IV administration normally either requires a less efficient near instantaneous bolus therapy or else the usage of numerous vials of different medications.

In the clinical setting, long-time-period doses of IV medication has proven extremely effective, however, not all patients may be able to use a system which requires them to go to a clinic repeatedly over the course of a week and remain for hours at a time. Thus clinically, it may be necessary to find a less effective treatment which is simply easier to administer. Enteral administration of one type or another immediately becomes a consideration, despite the poor condition of the stomach and intestinal lining of the substance abuser, if the enteral administration is effective in overcoming other barriers to efficient metabolization.

In addition, a combinational therapy in which a first long term IV formulation is used in the clinical setting followed by a second longer term oral formulation is believed to offer the best therapeutic benefits of both routes of administration.

Workers serving the needs of patients addicted to substance abuse can see the effects of these barriers to efficient usage of medications—practical barriers which the various researchers exploring the complexities of the neural pleasure/addiction processes may tend to deprecate or even overlook. At the same time, clinical workers and patients tend to value ease of administration and long shelf life of medications and thus tend to favor oral medications or substances which can be injected by means of a short-term bolus under pressure. The present invention concerns taking high effectiveness long term IV solutions and applying them in the regime of oral administration.

"Metabolic by-pass" is crucial to the invention, this term includes by-pass of the liver ("liver by-pass"), minimal use of the pancreatic juices, and the ability to cross the blood/brain barrier without reliance on metabolic resources. Agents are selected based upon their ability to by-pass metabolic processes. In particular, forms of the agents which can best by-pass metabolic processes are selected over forms which do not so easily do so. Forms of agents which require reduced metabolization, ideally, no metabolization, by the body of the patient are also called "active agents", "cellularly active" or "cellularly active agents" herein. The phrase "minimal metabolic processing" as used herein falls within the overall term "metabolic by-pass" and refers to a situation in which the disclosed and claimed metabolic by-pass is only partial, and some degree of metabolization is not avoided. Such minimal metabolic processing or minimized metabolic processing or reduced metabolic process is nonetheless described by the therm "metabolic by-pass" as used herein.

Liver diseases most commonly associated with alcohol abuse strike the liver of users of many commonly abused substances. The liver filters out toxins, be they ethanol, cocaine metabolites, anabolic steroids, or any other substances. The results are cirrhosis and fibrosis, (gradual replacement of liver tissues with fat and connective matter), hepatitis and inflammation, portal hypertension, infection of the lobules, and other conditions. The net result is badly degraded liver function, resulting in difficulty metabolizing amino-acids and vitamins which the liver of a healthy individual would not have any difficulty breaking down into the proper form. Substance abusing individuals also generally suffer from poor nutrition and a low metabolic energy level which may not be up to the task of suddenly efficiently metabolizing a number of medicinal agents if administered orally, or up to the task of suddenly metabolizing agents administered intravenously if such agents are not provided in their final metabolically active or cellularly active form (or a form as close to that final form as possible), or even up to the task of metabolizing agents which are administered in a very short time frame (i.e. via short-term bolus). For example riboflavin (a B2 vitamin), an ingredient in known anti-craving medications, is normally absorbed by the intestinal lining and then metabolized by the liver into riboflavin-5-phosphate, the cellularly active form used by the body in neural functioning. Riboflavin-5-phosphate is a water soluble form which passes the blood/brain barrier. But very importantly, since riboflavin must be metabolized by the liver into riboflavin-S-phosphate before being usable, and since the typical substance abuser has liver damage, the efficacy of administered riboflavin is reduced. In addition, the substance abuser typically needs a prompt reduction in the physiological craving. Requiring metabolization of riboflavin by the liver not only reduces the impact of the riboflavin and requires metabolic energy, it also slows down the onset of the craving reduction. The difference between oral and IV administration may not be significant in the context of liver function, because even parenteral administration of riboflavin via a direct injection of a short-term bolus to the patient does not alter the requirement for liver function to produce the form of riboflavin actually required. Yet since metabolization of riboflavin is a trivial task for a healthy liver, researchers have tended to overlook the entire issue. In addition, riboflavin-5-phosphate is not absorbed orally, a fact which militated against use of riboflavin-5- phosphate in known anti-craving medications. Selection of the riboflavin-5-phosphate form of riboflavin as taught by the present invention allows liver by-pass by the medication, that is, the medication is already in the form needed by the body of the patient, without liver interaction. Selection of this form provides blood/brain barrier bypass and also provides greater effectiveness of the administered substance: to achieve an equivalent effect, 40 times as much riboflavin as riboflavin-5-phosphate must be administered and the body must metabolically process it, mostly in the very organ, the liver, which is usually hardest hit by substance abuse. Thus the present invention teaches the use of this better form of the substance. It may be seen that the overall metabolic by-pass may comprise several steps, one of which is avoiding the use of substances which must be metabolized in the liver, referred to as "liver by-pass" herein.

Niacin (vitamin B3), another agent commonly employed in anti-craving medications, also requires metabolization by the liver into the water soluble form which passes the blood/brain barrier and is converted more quickly into stronger forms used in the brain. The present invention's teaching is that the combination of agents for the medication should be selected so as to avoid being inefficiently used due to damage to the body (especially the liver, in the case of niacin) of substance abusing individuals. This teaching leads, as in the case of riboflavin, to the concept that liver involvement should be avoided, which in turn leads to the conclusion that the metabolite of the niacin which actually reaches and is used in promotion of amino-acid levels in the brain, that is, niacinamide, should be given directly, thus avoiding reliance on the (possibly dysfunctional or malfunctional) liver, reducing the drain on the metabolic resources of the patient, reducing the time required for the active form of the agent to reach the blood supply and increasing the period of time during which both the niacinamide and the amino-acids whose travel to the brain it promotes are simultaneously available in the blood supply. Inositol, another B3 vitamin, also is selected on this basis.

Glutamine is another example of an agent, in this case an amino-acid, for anti-craving formulas which under the teaching of the present invention should be replaced with L-glutathione in IV formulations. L-glutathione is useful as a single tripeptide in quenching/rescuing free radicals that interfere with normal cell metabolism. It prevents brain damage. It also increases levels of the neurotransmitter GABA; GABA promotes dopamine and other neurotransmitters. Thus, L-glutathione has properties which are very useful in anti-craving therapy. However, L-glutathione's use in anti-craving medications is believed to be unique and non-obvious for one of the same reasons which will be reiterated in relation to other amino-acid forms, vitamin forms and mineral forms used in the invention. Specifically, while L-glutathione is the cellularly active, "final form", or metabolite, which is actually used in neurochemistry of the brain, glutamine is the form which can absorbed after oral administration to the body of a healthy human being, and thus the form taught by the prior art. Giving an individual "off-the-shelf" glutathione would merely increase the metabolic load on the patient's body, which would be forced to reduce it to glutamine, at the time of ingestion, absorb it, then metabolize it internally into the desired L-glutathione. In order to provide the body with this beneficial agent and yet provide metabolic by-pass, the invention teaches that L-glutathione must be used instead of glutamine and that the PH must be balanced. Normally, L-glutathione has a PH of between 2 and 3 and is not usable. At the time of compounding of the present invention, the L-glutathione must have its PH increased in order to remove a sulfur molecule. While it is necessary to increase the PH above roughly 6 (a value which may be dependent upon technique used) in order to remove the sulfur molecule, at a PH above 7.2 the L-glutathione itself breaks down.

In the present oral formulation of the medication, the use of glutamine is once again desirable because glutathione is not absorbed orally. It will be understood that oral formulation of metabolic bypass products will require use of forms of aminos, minerals and vitamins which are absorbed orally with reasonable efficacy and minimal energy use by the patient's body.

Metabolic by-pass of stomach lining, intestinal lining, liver and pancreas function also guides the selection of methylcobalamin, a water soluble and cellularly active metabolite of vitamin B12 which passes the blood/brain barrier. Normally, this form must be manufactured from inactive forms in the liver. Cyanocobalamin, the orally administered form, is first absorbed through the intestinal lining/stomach lining, and then converted by the liver to hydroxy-cobalamin. The hydroxy-cobalamin form is then converted, again by the liver, to the cellularly active methyl-cobalamin. Because cyanocobalamin is the form absorbed by the stomach/intestinal linings of healthy individuals (and of course, absorbed at a reduced efficiency by substance abusing patients) it is the form taught in the references. The present invention teaches that metabolically by-pass is desirable, as well as avoiding the double load on the liver, so while cyanocobalamin may be used in the oral formulation it is to be avoided in the intravenous formulation.

Diseases of the stomach lining and intestinal lining are also quite common in substance abusers. Alcohol releases free radicals on ingestion, in addition to the toxic effects of ethanol and other substances in alcohol. Even those who abuse substances self-administered by injection often experience such symptoms, due to the strong correlation between abuse of "schedule" substances and abuse of alcohol, which is known to injure the stomach/intestinal lining(s). In addition commonly abused substances other than alcohol also harm the stomach lining, by such mechanisms as gastritis (inflammation of the intestinal and stomach linings) and ulceration. Bleeding lesions, colitis and various cancers are further consequences of substance abuse suffered by the digestive tract and its linings. The extreme physiological stress often brought on by the impact on the individual's life caused by their substance abuse problem also leads to these forms of stomach and intestinal damage. Non-steroidal anti-inflammatory drugs (NSAIDs), commonly over-used by sufferers from most forms of substance abuse, also cause stomach lining injury. Renal and liver failure also lead to damage to the stomach lining, and as discussed in the previous paragraph, liver degradation is a "normal" symptom of the abuse of a wide range of substances beyond alcohol, even commonly injected substances or substances absorbed through the mucus membranes. In addition, the malnutrition of such patients makes in incumbent that the medication "burn" as little as possible of the body's metabolic resources. Thus, the most efficient forms of the anti-craving substances are those which require the least metabolizing and offer the highest effect.

The time factor plays two further roles in guiding the selection of agents (amino-acids, vitamins, and minerals) for use in the medication. First, the agents chosen should be available to the patient's body at approximately the same time. For example, a synergistic effect of L-tryptophan, magnesium and riboflavin-5-phosphate is desired, meaning that it is counterproductive to allow one or more of the three agents arrive at a different time from the other agents. Selecting the forms necessary to achieve the correct time of metabolization, as taught by the present invention, assists in making sure that the agents are simultaneously present in the desired systems at the desired times. Providing administration over a period longer than a single bolus also acts to keep the desired mixture of biochemicals in simultaneous circulation, which is an advantage of either longer term IV drips or repetitive enteral administration. At the same time, it is desirable to provide some limit on the length of time and amount of effort required for administration. The second time issue related to clinical needs is the speed with which the medication takes effect. The oral formulation of the present invention allows for faster self-administration by patients, hopefully assisting in avoiding emergencies and providing a more convenient method of administration, thus hopefully increasing the reliability of patient usage. In addition a "metabolic time lag", unpredictable even in an individual with a healthy metabolic system, can be minimized or avoided. (It is also worth mentioning the background datum that intravenous administration is normally faster than oral administration. The success of the present invention when orally administered is thus gratifying.)

Once again, a delicate balancing of the time factors is required. The fastest possible administration (that is a single injection or a fast series of injections) is highly likely to result in having different agents, which are supposed to be acting synergistically, to arrive in the blood stream and brain at different times. So while it is desirable to provide the fastest possible onset, it is also desirable to make sure that the speedy onset is not bought at the price of non-simultaneous arrival of the biochemicals. As an example, if a single injection is given containing both riboflavin and L-tryptophan, the riboflavin must undergo metabolic action by the liver before it can assist the L-tryptophan's action. But the L-tryptophan concentration in the blood and brain will start to go down almost instantly after injection. Obviously, the riboflavin should be directly usable, and the two should be administered over a sufficient period of time for maximum combined concentrations to exist. Thus IV administration is one favored technique, but oral administration in the corrective role may also allow reasonable period of time for the two agents to be present simultaneously.

Finally, addition of oral therapy as a follow-up to clinical corrective long term IV drip formulations offers benefits of both higher initial efficacy and longer term maintenance of desirable substances.

Figure 2:
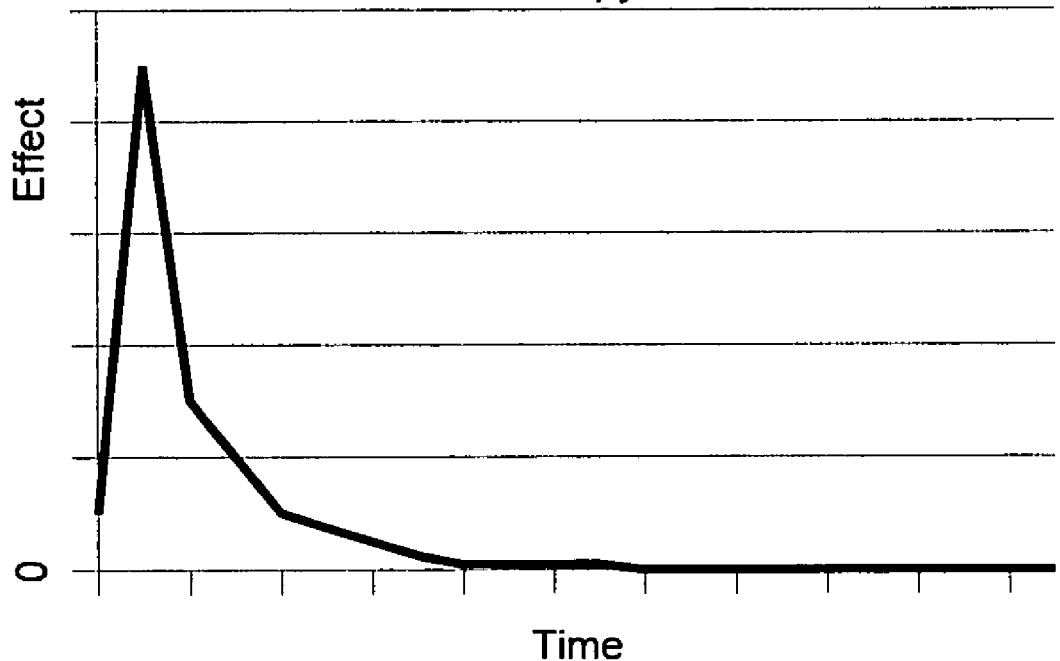

FIG. 2, PRIOR ART, is a graph of the effectiveness of short-term bolus therapy as measured by concentrations of active agents versus time.

The effectiveness of an agent is a function of at least two factors: instantaneous effectiveness, which depends upon concentration, and the length of time for which that instantaneous effectiveness (concentration) is maintained. Thus, instantaneous effect tracks concentration, but overall effectiveness depends on an integration of instantaneous effect with respect to time. Viewed graphically, this is easy to measure: the area under the graph of concentration's instantaneous effectiveness, integrated across time is the overall effectiveness of the agent being examined.

Concentration may be taken a number of ways: concentration in the brain fluids, concentration in the blood stream (not as accurate but considerably easier to measure) or other concentrations, i.e. versus the body mass of the individual.

FIG. 2 depicts the effectiveness of a single fast administration of an agent to a patient. This fast administration may be by several methods but is described as being short term bolus injection to the circulatory system. In other words, a needle and syringe with medication is being inserted into a blood vessel and the plunger is pushed with sufficient pressure to force the medication through the cannula of the needle into the blood vessel against the internal pressure of the human circulatory system. Such administration typically requires only a few seconds, which is in all likelihood one reason the prior art teaches in this direction. The bolus of medication will thus arrive in the system over the course of mere seconds. In the event of oral administration on the other hand, the effect is slower but the overall shape of the graph is not significantly changed.

FIG. 2 shows the result in terms of instantaneous effect of the medicinal agent: a fast "spike" of very high value, then a rapid and asymptotic decline to a value near zero. The shape of the decline is determined essentially by the half life of the agent in the human body, and the desire for longer half-lives may have led prior-art researchers to avoid forms of agents which were highly soluble.

The overall effectiveness of the medication, the area under the graph line, is actually fairly limited. There is an extremely short time of extremely high concentrations (presumably, as high as good medical practice allows) and then a short period of very low levels during the asymptotic decline.

Figure 3:
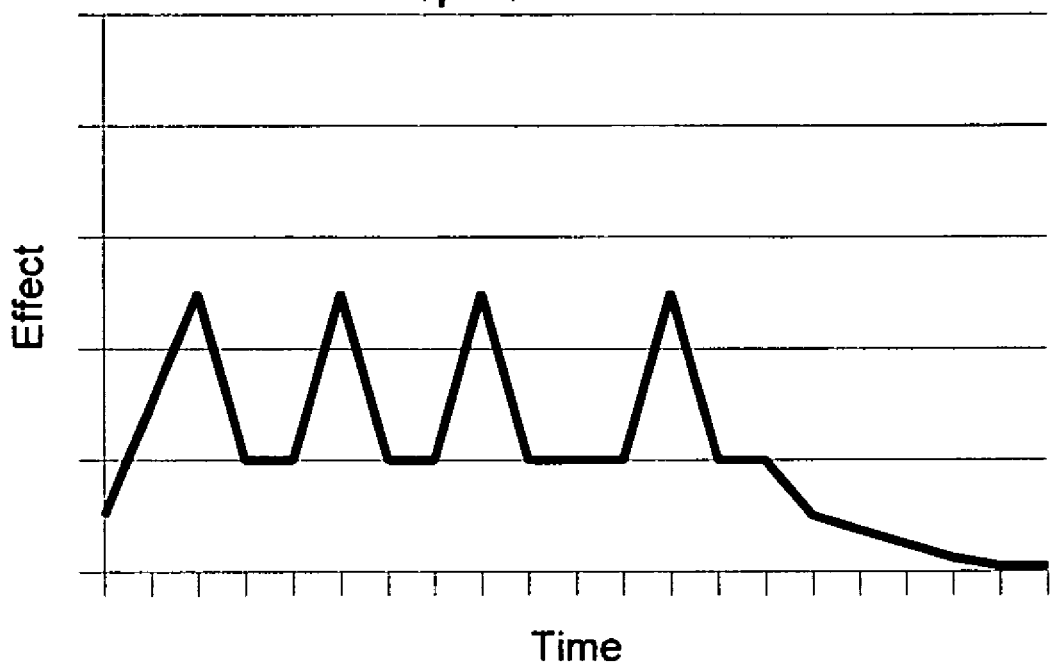
FIG. 3 is a graph of the effectiveness profile of repetitive oral administration therapy in terms of concentrations of active agents versus time, for a first concentration and period of administration.

FIG. 3 is a graph of effectiveness profile of the present invention administered via repetitive oral administrations. Instead of a single fast administration, a plurality of enteral administrations occur, each one slightly slower than the single bolus and the cumulative total of the administrations being much higher than a single bolus injection. The result is a modestly prolonged administration. The timing of such an administration can be adjusted by adjusting the timing and dosage of the medication. Thus FIG. 3 depicts a very oral convenient administration if the formulation to patients: IV therapy longer periods of time, while believed to be more effective, is found to be less clinically practical for some patients, who may not have sufficient time available to the task.

FIG. 3 shows that the area under the graph is greatly expanded by this technique. The initial "spike" is repeated, so that the overall effectiveness (concentration times time) achieves higher levels as a function of time.

FIG. 3B shows the effectiveness profile of an increased concentration of the invention administered for a period of time equivalent to that of FIG. 3. The effect of the therapy is greatly increased for that period of time. In clinical trials, the applicant has determined that extended periods of administration are preferable and more effective. Thus, a greatly increased period of administration, not just moderately prolonged but actively prolonged for an extended period of time, is preferred. It is also noted that certain extremely practical limits pertain to the increased concentration approach. Firstly, as with a "bolus" type administration, the amount of the therapy which may be administered is limited by the necessity to avoid over dosage of the patient. Obviously, at some level, the various compounds of the invention cease to be beneficial.

More subtly, however, the substances of the invention have certain maximum useful rates of metabolization. Administration of an amount in excess of that which can be usefully metabolized merely represents an extra strain on the system of the individual being treated. Of course there is no point in administering amounts beyond that which the human body can metabolize and use. More importantly, as noted, the bodies of most substance abuse disorder patients have severe chronic inability to metabolize substances as efficiently as is nominal. The first result is of course the need for metabolic bypass, but in addition, it would be desirable to avoid administering amounts during courses of time which would preclude use and would instead require disposal of the excess.

Thus, the chart of FIG. 3B is shown as reaching a "metabolically useful maximum level" at which it cannot be effectively increased. Thereafter, the concentration may be maintained but there is little purpose to increase beyond that metabolically useful level.

On the other hand, increases in the length of time of the administration also eventually reach a point of diminishing returns, and more importantly, reach a point of complete impracticability in which the patient simply no longer has time available for the protracted therapy.

FIG. 3C brings all of this together. In the presently preferred embodiment and best mode now contemplated, the maximum metabolically useful level is achieved. However, as with the embodiment of FIG. 3A, the increased concentration of the oral therapy is maintained for a prolonged period of time. In practice, almost indefinite periods of time, days and even weeks, are achievable for motivated or monitored patients in the out patient clinical setting, and thus achieves the maximum efficiency in providing to the patients the desirable metabolically useful combination for an extended period of time. By means of this embodiment, the patient's body is able to hit a high level of useful metabolic activity of the compounds which decrease craving, pain, and other symptoms of the addiction, and is able to maintain this desirable state for a prolonged period of time. Note that a daily administration, for example times daily at a dosage of three of the units of medication (or otherwise repeated once or multiple times daily for a period of days or weeks), results in a patient having the desirable levels within their system for a large percentage of the complete daily cycle.

FIG. 4, PRIOR ART, is a graph of the effectiveness of three agents having differing metabolic half-lives when administered simultaneously, as measured by concentrations of the agents versus time.

While FIG. 2 and FIG. 3 simplified the actual anti-craving medication to a single active agent, FIG. 4 addresses the fact that such medications may well be several agents. In FIG. 4, a single fast administration (for example of one short term bolus, or a single oral administration) is shown, with the instantaneous effectiveness of three different agents shown.

As stated previously, the brain's neurotransmission system is quite complex, featuring large numbers of interrelationships of neurotransmitters, pro-neurotransmitters, amino-acids, minerals, vitamins, and metabolites of these, all acting simultaneously on various different areas of the brain. Thus, anti-craving medications may have several agents which attempt to achieve the necessary synergistic effects in the brain, that is, all agents should be present, at the right time and in the proper, cellularly active forms, for maximum effectiveness. The synergistic effects of having, for example, a pro-neurotransmitter, a mineral helpful for its passage of the blood/brain barrier, and a vitamin which regulates the enzymes which break down the desired neurotransmitter are well recognized. FIG. 4 shows the results of a single fast administration of agents NOT selected for metabolic by-pass based upon the special needs of substance abusing patients.

The "fast agent" may be taken to be an agent which is absorbed quickly, perhaps even in the stomach, or after short term bolus injection requires no metabolization. The "medium term agent" may be taken as an agent which is absorbed more slowly, or must be metabolized by the liver into the cellularly active form, or is slow to cross the blood/brain barrier, or is otherwise delayed in reaching the brain or bloodstream in the proper form for use thereby. The slow term agent may be an agent which is absorbed very slowly, or perhaps requires multiple steps of processing by the liver in order to achieve the cellularly active form, or otherwise is delayed more than the other two agents in reaching the brain or bloodstream in the proper form for use therein.

In FIG. 4, there is a clear reduction in the overlapping area under the three graph lines, representing the overall effectiveness of the required synergistic effects. At the time the fast agent is present in high concentrations, the other two agents are not yet heavily bioavailable, or may be bioavailable in the blood stream when they are needed in the brain. At the time of the medium term agent's maximum availability, there is a slowly increasing supply of the slow agent and a slowly dwindling supply of the fast agent, but this phase, if it actually exists at all in practice, quickly gives way to the time frame when both the fast and medium term agents are in low concentration and the slow agent is readily available.

Thus, it is preferable to continuously supply the multiple required agents and thus guarantee their bioavailability in the blood stream and their availability in the brain. For this reason, the frequent oral administration approach is used with the formulation previously found to be effective in the long term IV administration.

Finally, it is considered important to ensure that patients take a series of doses of regular size, rather than occasional large doses. Occasional large doses administered in a mode (bolus therapy) which encourages very fast metabolization may have the undesirable effect of a new spike of high concentration inflicted on the body of the patient at each bolus. While the net effect is a theoretical improvement of the area under the chart (instantaneous effectiveness as function of instantaneous concentration, integrated over time), the presence of the spikes makes the likelihood of systemic overload more likely.

It should be noted that in alternative embodiments of the invention, the selected active agents are administered sequentially via IV drip and thus metabolic by-pass is still achieved. The IV drip administration is still used as part of the metabolic by-pass (i.e. by providing fast acting water-soluble forms which do not require absorption or liver action), but the effect described above of extremely prolonged simultaneous bioavailability via multiple oral administrations is not utilized.

Another factor relating to selection of ingredients for anti-craving medications is the ease of the combined ingredients crossing the blood/brain barrier. The poor nutrition of substance abusers is believed to negatively impact the ability of active agents to cross the blood/brain barrier. While getting the active agents into the patient's blood stream ("bioavailability") quickly is itself a victory, it is equally important to choose a combination of agents which promote crossing of the blood/brain barrier. As alluded to earlier, some prior art medications contain fructose, glucose, calcium or other agents which actually have mixed results in assisting a broad spectrum biochemicals across the blood/brain barrier. Tryptophan, for example, has a lower affinity than other amino-acids for the protein which carries the amino-acids across the blood/brain barrier, and furthermore the poor nutrition of many substance abusers tends to result in a comparatively low concentration of tryptophan in the blood in any case.

One known solution is to use calcium to drive the "competing" amino-acids out of the blood stream and in to the muscles, but this solution is only optimum if tryptophan is the only amino-acid of interest, in the present invention, tyrosine is also used, as it is a precursor to dopamine. The amount of tyrosine used is a factor of the maximum amount that can be administered without driving dopamine levels too high (or spiking them) and the limit placed on its use by its solubility.

The present invention teaches that in medications in which it is desirable to assist a number of amino-acids across the blood/brain barrier, it is preferable to omit calcium when selecting the ingredients of the medication, or else to limit calcium intake (128 mg. suggested for the oral formulation of the present invention). On the other hand, the known action of chromium in unbinding tryptophan from albumin in the blood in order to increase the concentration of tryptophan available for transport across the blood/brain barrier makes it another and more suitable selection, based upon the special nutritional deficiencies of substance abusing patients, so the calcium is supplemented with chromium to enhance acceptance of amino-acids by the brain of the patient.

In addition to the teaching of the present invention to avoid or in oral formulations to minimize the use of calcium (which is present in some lower concentration in the body in any case, even in a reduced concentration in the bodies of nutrition-deficient substance abusers) the present invention teaches that in anti-craving medications it is desirable to avoid not just the calcium itself but also forms of other agents which will release calcium. As another specific application of the present invention's teaching of the desirability of metabolic by-pass, pantothenic acid (i.e. D-calcium pantothenate) (broadly vitamin B5) should be avoided, as it will release calcium after administration. Accordingly, pantothenic acid is minimized in use even in the oral formulation of the invention (25 mg) so as to gain what benefits of the vitamin which may be gained, while the IV formulation eschews this use entirely.

Obviously, crossing of such barriers as the blood/brain barrier is greatly facilitated by prolonging the period of administration. In clinical trials, the applicant has determined that extended periods of administration are preferable, and without wishing to be bound by any particular theory, it is believed that part of this is due to the fact that the combination ingredients, provided for an extended period of time provide a much greater opportunity for crossing the blood/brain barrier.

One final barrier to effective use of anti-craving medications is not premised upon the state of the patient's health but rather upon the practicality of administration of the medication. When providing multiple medical agents to patients, the greater the number of components to be administered, more difficulty in administration, the greater the resistance of the patient to the therapy, and the greater the commitment of health-care professional time necessary to begin the administration of them. In addition medical solutions containing multiple active ingredients must be carefully compounded to avoid engendering new problems. Different active ingredients may react with each other in unpredictable ways inside the vials of medication during storage. One problem is precipitation of the agents in the liquid medication, calcium, in addition to its other undesirable properties, is prone to precipitation. Another problem is direct reaction of the agents with each other. A sister problem with multiple agent formulas is chelation, that is, metallization of another product such as a carbon-based molecule. The resulting precipitated or combined or metal-organic chemical or salt usually no longer has the desired medicinal properties, may no longer be suitable (small enough) to pass through the cannula of the IV needle, and may even be dangerous to the patient if administered. Other reactions can occur.

When several agents are compounded together into one component of the medication, as in the present invention, the shelf-life of the product dwindles sharply. Light hastens this process markedly and temperature has a similar important impact on shelf-life. Thus visual inspection is required before use by medical personnel, in order to verify that the product remains safe for use. These disadvantages are overcome by the intravenous formula of the present invention to the extent that a reasonable shelf-life on the order of 30 days is attained. Stability is another factor which has guided prior art research away from anti-craving medications for IV drip administration featuring active agents in the forms most useful to the body of the typical substance abuse patient. For the oral formulation taught herein, the issue is circumvented entirely: capsule form medications may be stable for months or years depending upon storage conditions and other factors.

Glucose and fructose solutions are not feasible for use in administering via IV drip multiple amino-acid medicines, and they are not necessarily suitable for the oral formulation of the present invention. First, the sugars "spike" the levels of the neurotransmitters in the brain much like the abused substance (sugar is often considered to be an abused substance itself quite apart from the fact that alcohols are sugars), thus included sugars would function as "agonists", reducing the craving temporarily by briefly satisfying it rather than by returning the brain to normal functioning. Second, fructose and glucose act (much like calcium does), possibly driving amino-acids into the muscle tissues rather than across the blood/brain barrier, and furthermore this undesirable activity is promoted by the presence of chromium which is an important agent for other reasons previously discussed.

A further important issue which arises form the improved selection process for the agents in anti-craving medications is the criteria for exclusion of potentially beneficial agents by reason of the negative effects on the efficacy of the overall medication. Sugars are also to be avoided under the teaching of the present invention, and glutamine has been found to reduce sugar cravings. Since glutathione breaks down and is not absorbed effectively by the intestines, glutamine becomes a preferred choice.

Obviously the medication must be administered in a dose sufficient to reduce craving by an individual for the abused substance they crave, for purposes of this document, the phrase "reduce craving" is taken to mean any degree of craving reduction whatsoever.

In addition to the usual factors which impact any dosage calculation for any patient, dosage calculation of the present medication depends upon a number of factors which relate specifically to substance abusing patients. The patient's degree of longitudinal sobriety is of primary importance: a patient who is still presently abusing the addictive substance will receive medication on a daily basis while those patients who have avoided substance abuse for a period of time will be on a maintenance regimen and will receive medication at a intervals of greater than one day. The second factor to consider is that of withdrawal symptoms: when the patient is in withdrawal from substance abuse, the need for anti-craving medication is obviously much greater. A third factor to consider is the presence of co-morbid health conditions, the fourth issue goes along with this: is the patient in pain, suffering from cancer or preparing for scheduled surgery. At least one of the agents of the present invention will reactivate dormant tumors which patients may have if the dosage is not proper; thus it is important to question patients carefully on all of these factors. Fifth, blood profile is of vital concern. Does the patient show signs (or test positive) for Hepatitis A, B or C, HIV, or do they show elevated liver enzyme levels? Finally, the patients use or abuse of other medications and allergies, while a standard medical question, is especially relevant to the substance abusing patient who may be sick and therefore properly receiving other medications or may be self-administering substances of their own choice.

Based upon such factors, the timing of the dosages, the strength of the dosages and the concentrations may be adjusted. In addition, it is also possible to adjust the formula for differing needs of differing individuals; the example of tyrosine is explained herein.

The formula of the a first embodiment is as follows:

TABLE ONE

| INGREDIENTS PER CAPSULE OF ORAL FORMULATION | |
|---|---|
| DL-PHENYLALANINE | 375 MG |
| L-TYROSINE | 375 MG |
| L-GLUTAMINE | 375 MG |
| GABA | 51 MG |
| 5-HYDROXYTRYPTOPHAN | 30 MG |
| DL-METHIONINE | 30 MG |
| VITAMIN C | 15 MG |
| THIAMINE | 1 MG |
| RIBOFLAVIN | 1 MG |
| PYRIDOXINE | 7 MG |
| FOLIC ACID | 99 MCG |
| CYANO-COBALAMIN | 26 MCG |
| BIOTIN | 7 MCG |
| PANTOTHENIC ACID | 25 MG |
| CALCIUM | 128 MG |
| CHROMIUM | 22 MCG |
| MAGNESIUM | 25 MG |
| ZINC | 25 MG |
| MANGANESE | 188 MCG |

As noted, the timing of the dosages, the strength of the dosages and the concentrations may be adjusted. In particular, as noted in reference to FIGS. 3 through 3C, increases in dosages up to some limit of metabolic usability may be contemplated. Doubling of the above formulation still produces a formula within the limits of metabolic usefulness imposed by the body of a patient suffering from SAD. Thus, the formula for a second, presently preferred embodiment, is as follows:

TABLE TWO

| INGREDIENTS PER CAPSULE OF ORAL FORMULATION | |
|---|---|
| DL-PHENYLALANINE | 125 MG |
| L-TYROSINE | 125 MG |
| L-GLUTAMINE | 125 MG |
| GABA | 17 MG |
| 5-HYDROXYTRYPTOPHAN | 10 MG |
| DL-METHIONINE | 10 MG |
| VITAMIN C | 7.5 MG |
| THIAMINE | 500 MCG |
| RIBOFLAVIN | 500 MCG |
| PYRIDOXINE | 3.5 MG |
| FOLIC ACID | 50 MCG |
| CYANO-COBALAMIN | 13 MCG |
| BIOTIN | 3.5 MCG |
| PANTOTHENIC ACID | 12.5 MG |
| CALCIUM | 64 MG |
| CHROMIUM | 11 MCG |
| MAGNESIUM | 12.5 MG |
| ZINC | 12.5 MG |
| MANGANESE | 94 MCG |
| SIBERIAN GINSENG | 2.5 MG |
| GOTU KOLA | 2.5 MG |
| DMAE | 2.5 MG |
| MUCUNA PRURIENS | 2.5 MG |
| RHODIOLA | 2.5 MG |

Of course, the original limitation remains in place: the ingredients selected must provide an effective anti-craving medication when they finally reach the brain. But the selection of the ingredients should be modified based on the teaching of the present invention. As one example, copper, pyridoxine and ascorbic acid may be present in the oral medication in order to facilitate the conversion of tryptophan to serotonin, while magnesium facilitates the bonding of the serotonin to the neural receptors—but it is the teaching of the present invention that cupric sulfate, pyridoxal-5-phosphate mono-hydrate, sodium salt ascorbic acid from a beet source, and magnesium chloride are the particular forms selected for maximum efficacy in the intravenous setting and under the disadvantageous conditions in the metabolism of the typical anti-craving patient. Pyridoxal-5-phosphate mono-hydrate, for example, is many times as powerful (possibly hundreds of times as powerful) as the pyridoxal HCL used in prior art references: pyridoxal-5-phosphate, the cellularly active metabolite, could not be absorbed orally (it would be broken back down to the pyridoxal HCL for absorption, then metabolized internally, in the liver, into the desirable form) and thus the prior art taught away from this cellularly active agent of the present invention. For the oral formulation, pyridoxine is used in order to allow efficient absorption in the liver.

TABLE THREE

| INGREDIENTS PER CAPSULE OF ORAL FORMULATION | |
|---|---|
| DL-PHENYLALANINE | 125 MG |
| L-TYROSINE | 125 MG |
| L-GLUTAMINE | 125 MG |
| GABA | 17 MG |
| 5-HYDROXYTRYPTOPHAN | 10 MG |
| DL-METHIONINE | 10 MG |
| VITAMIN C | 7.5 MG |
| THIAMINE | 500 MCG |
| RIBOFLAVIN | 500 MCG |
| PYRIDOXINE | 3.5 MG |
| FOLIC ACID | 50 MCG |
| CYANO-COBALAMIN | 13 MCG |
| BIOTIN | 3.5 MCG |
| PANTOTHENIC ACID | 12.5 MG |
| CALCIUM | 64 MG |
| CHROMIUM | 11 MCG |
| MAGNESIUM | 12.5 MG |
| ZINC | 12.5 MG |
| MANGANESE | 94 MCG |
| SIBERIAN GINSENG | 5 MG |
| GOTU KOLA | 2.5 MG |
| DMAE | 2.5 MG |
| MUCUNA PRURIENS | 2.5 MG |

Certain agents may be substituted for one another in embodiments of the invention. Other changes may be made.

Phenylalanine is known to reduce enzymatic destruction of neurotransmitters—it is the further teaching of the present invention that D-phenylalanine and L-phenylalanine may be preferable to the racemic DL-phenylalanine previously used, as the oral administration allows use of greater quantities in order to achieve the desirable levels in the blood.

In general, it is important to understand that the phrase "selection of forms" of active agents can thus refer not only to forms having different chemical formulas and different chemical names but also to forms which are isomers of each other. However, the active agents taught by the present invention are selected for reasons primarily related to the goal of effective use by the substance abusing patient's body. The preference for beet source ascorbic acid (vitamin C) is based on the potential for allergic reactions of patients to the normal corn source ascorbic acid, this is also a factor in avoiding the use of preservatives in the medicine. The conversion to a sodium salt is preferable for the same reasons discussed in regard to folic acid: a water soluble form passing the blood/brain barrier, elimination of need for sodium addition in stomach, etc.

Thiamine HCL is also a water soluble B vitamin which passes the blood/brain barrier. While the forms of these active agents which the present invention teaches are water soluble and pass the blood/brain barrier, other additional forms of these agents exist and may be used, which equivalent forms are relatively water soluble and/or also pass the blood/brain barrier.

This is yet another reason for the pains taken in selection and compounding of the present invention: the bodies of substance abuse patients are more prone to side effects, allergic reactions, other negative responses to medications. Consistent selection of active agents which avoid such reactions makes the present invention both superior to and admittedly more difficult to develop, compound, store and use than prior art medications. However, the present invention provides a medication with the bodies of substance abuse patients can more practically use with high efficiency.

All of the minerals must be administered in the proper ratios: in the wrong ratios, they will promote accumulation or disturb the natural balance of the nutrients they are designed to promote. Excess amounts may even suppress enzymatic functions rather than promote them.

A multiple component long term IV drip therapy may be used as a preliminary portion of the medication.

The formula of the a first embodiment of a long term IV drip therapy portion of the medication is as follows:

TABLE FOUR

The first component comprises:

approximately 3.75 grams of D-phenylalanine,
approximately 3.75 grams of L-phenylalanine,
approximately 0.025 grams of L-tyrosine,
approximately 1.2 grams of L-tryptophan,
approximately 7.5 grams of L-glutathione, and
water to bring the total volume to 1000 milliliters.
The second component comprises:

approximately 1 gram of folic acid,
approximately 0.2 grams of methylcobolamin,
approximately 250 grams of ascorbic acid from a beet source,
approximately 2.5 grams of thiamine hydrochloride,
approximately 0.2 grams of pyridoxal-5-phosphate monohydrate,
approximately 0.2 grams of riboflavin-5-phosphate sodium,
approximately 5.0 grams of niacinamide,
approximately 10 grams of dexpanthenol,
approximately 5 grams of inositol, and
water to bring the bulk volume to 1000 milliliters.
The third component comprises:

approximately 4 grams of magnesium chloride,
approximately 6.4 grams of zinc sulfate,
approximately 0.786 grams of cupric sulfate,
approximately 0.308 grams of manganese sulfate,
approximately 0.01026 grams of chromic chloride,
approximately 0.0196 grams of sodium selenite, and
water to bring the bulk volume to 1000 milliliters.

As noted, the timing of the dosages, the strength of the dosages and the concentrations may be adjusted. In particular, increases in dosages up to some limit of metabolic usability may be contemplated. Doubling of the above formulation still produces a formula within the limits of metabolic usefulness imposed by the body of a patient suffering from SAD. Thus, the formula for a second, presently preferred embodiment, is as follows:

TABLE FIVE

The first component comprises:

approximately 7.50 grams of D-phenylalanine,
approximately 7.50 grams of L-phenylalanine, TABLE FIVE-continued approximately 0.05 grams of L-tyrosine,
approximately 2.4 grams of L-tryptophan,
approximately 15.0 grams of L-glutathione, and
water to bring the total volume to 1000 milliliters.
The second component comprises:

approximately 2 grams of folic acid,
approximately 0.4 grams of methylcobolamin,
approximately 500 grams of ascorbic acid from a beet source,
approximately 5.0 grams of thiamine hydrochloride,
approximately 0.4 grams of pyridoxal-5-phosphate monohydrate,
approximately 0.4 grams of riboflavin-5-phosphate sodium,
approximately 10.0 grams of niacinamide,
approxiMately 20.0 grams of dexpanthenol,
approximately 10.0 grams of inositol, and
water to bring 'the bulk volume to 1000 milliliters.
The third component comprises:

approximately 8 grams of magnesium chloride,
approximately 12.8 grams of zinc sulfate,
approximately 1.572 grams of cupric sulfate,
approximately 0.612 grams of manganese sulfate,
approximately 0.02052 grams of chromic chloride,
approximately 0.0392 grams of sodium selenite, and
water to bring the bulk volume to 1000 milliliters.

Administration of an IV drip form may take from one hour to six hours, repeated daily for a period of one week to several weeks. One presently preferred embodiment is one four hour cycle per day for ten days, followed by administration of the oral formulation.

The present invention and the best mode presently contemplated thereof have been revealed so as to allow one skilled in the art to practice the invention without undue experimentation. While numerous details have been set forth for illustrative purposes, it will be obvious to those skilled in the art that the invention is susceptible to many equivalents, substitutions, and alterations without departing from the essential spirit and scope of the invention. Nothing in the foregoing disclosure is to be taken to limit in any way the scope of the invention, which is to be construed only on the basis of the appended claims.

What is claimed is:

1. An anti-craving oral medication for administration to the body of an individual suffering from substance abuse, the medication comprising:

| | |
|---|---|
| DL-PHENYLALANINE | 375 MG; |
| L-TYROSINE | 375 MG; |
| L-GLUTAMINE | 375 MG; |
| GABA | 51 MG; |
| 5-HYDROXYTRYPTOPHAN | 30 MG; |
| DL-METHIONINE | 30 MG; |
| VITAMIN C | 15 MG; |
| THIAMINE | 1 MG; |
| RIBOFLAVIN | 1 MG; |
| PYRIDOXINE | 7 MG; |
| FOLIC ACID | 99 MCG; |
| CYANO-COBALAMIN | 26 MCG; |
| BIOTIN | 7 MCG; |
| PANTOTHENIC ACID | 25 MG; |
| CALCIUM | 128 MG; |
| CHROMIUM | 22 MCG; |
| MAGNESIUM | 25 MG; |
| ZINC | 25 MG; |
| MANGANESE | 188 MCG; |
| GOTU KOLA | 2.5 MG; |
| DMAE | 2.5 MG; |
| MUCUNA PRURIENS | 2.5 MG; and |
| RHODIOLA | 2.5 MG. |

2. A multiple administration route anti-craving medication for administration to the body of an individual suffering from substance abuse, the medication comprising:
- a) a first course of intravenous therapy comprising:
  - a first component comprising:
    - 3.75 grams of D-phenylalanine,
    - 3.75 grams of L-phenylalanine,
    - 0.025 grams of L-tyrosine,
    - 1.2 grams of L-tryptophan,
    - 7.5 grams of L-glutathione, and
    - water to bring the total volume to 1000 milliliters;
  - a second component comprising:
    - 1 gram of folic acid,
    - 0.2 grams of methylcobolamin,
    - 250 grams of ascorbic acid from a beet source,
    - 2.5 grams of thiamine hydrochloride,
    - 0.2 grams of pyridoxal-5-phosphate monohydrate,
    - 0.2 grams of riboflavin-5-phosphate sodium,
    - 5.0 grams of niacinamide,
    - 10 grams of dexpanthenol,
    - 5 grams of inositol, and
    - water to bring the bulk volume to 1000 milliliters; and
  - a third component comprising:
    - 4 grams of magnesium chloride,
    - 6.4 grams of zinc sulfate,
    - 0.786 grains of cupric sulfate,
    - 0.308 grams of manganese sulfate,
    - 0.01026 grams of chromic chloride,
    - 0.0196 grams of sodium selenite, and
    - water to bring the bulk volume to 1000 milliliters; and
- b) a second course of oral medication comprising:
  - DL-PHENYLALANINE in the amount of 375 MG;
  - L-TYROSINE in the amount of 1375 MG;
  - L-GLUTAMINE in the amount of 375 MG;
  - GABA in the amount of 51 MG;
  - 5-HYDROXYTRYPTOPHAN in the amount of 30 MG; and
  - DL-METHIONINE in the amount of 30 MG.

3. An anti-craving oral medication for administration to the body of an individual suffering from substance abuse, the medication comprising:

| | |
|---|---|
| DL-PHENYLALANINE | 125 MG; |
| L-TYROSINE | 125 MG; |
| L-GLUTAMINE | 125 MG; |
| GABA | 17 MG; |
| 5-HYDROXYTRYPTOPHAN | 10 MG; |
| DL-METHIONINE | 10 MG; |
| VITAMIN C | 7.5 MG; |
| THIAMINE | 500 MCG; |
| RIBOFLAVIN | 500 MCG; |
| PYRIDOXINE | 3.5 MG; |
| FOLIC ACID | 50 MCG; |
| CYANO-COBALAMIN | 13 MCG; |
| BIOTIN | 3.5 MCG; |
| PANTOTHENIC ACID | 12.5 MG; |
| CALCIUM | 64 MG; |
| CHROMIUM | 11 MCG; |
| MAGNESIUM | 12.5 MG; |
| ZINC | 12.5 MG; |
| MANGANESE | 94 MCG; |
| SIBERIAN GINSENG | 2.5 MG; |
| GOTU KOLA | 2.5 MG; |
| DMAE | 2.5 MG; |
| MUCUNA PRURIENS | 2.5 MG; and |
| RHODIOLA | 2.5 MG. |

* * * * *